United States Patent
Lin et al.

(10) Patent No.: US 11,590,123 B2
(45) Date of Patent: Feb. 28, 2023

(54) OPHTHALMIC COMPOSITIONS

(71) Applicant: Aerie Pharmaceuticals, Inc., Bedminster, NJ (US)

(72) Inventors: Cheng-Wen Lin, Raleigh, NC (US); Casey Kopczynski, Chapel Hill, NC (US); Mitchell A. deLong, Chapel Hill, NC (US); Jill M. Sturdivant, Chapel Hill, NC (US); Ramesh Krishnamoorthy, Cary, NC (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 17/858,889

(22) Filed: Jul. 6, 2022

(65) Prior Publication Data
US 2022/0331308 A1    Oct. 20, 2022

Related U.S. Application Data

(63) Continuation of application No. 17/841,433, filed on Jun. 15, 2022, which is a continuation of application No. 15/691,607, filed on Aug. 30, 2017, now Pat. No. 11,389,441.

(60) Provisional application No. 62/382,237, filed on Aug. 31, 2016.

(51) Int. Cl.
| | | |
|---|---|---|
| *A61K 31/472* | (2006.01) |
| *A61K 9/08* | (2006.01) |
| *A61K 45/06* | (2006.01) |
| *A61K 47/02* | (2006.01) |
| *A61K 47/26* | (2006.01) |
| *A61K 9/00* | (2006.01) |
| *A61K 31/5575* | (2006.01) |
| *A61K 47/18* | (2017.01) |

(52) U.S. Cl.
CPC .......... *A61K 31/472* (2013.01); *A61K 9/0048* (2013.01); *A61K 9/08* (2013.01); *A61K 31/5575* (2013.01); *A61K 45/06* (2013.01); *A61K 47/02* (2013.01); *A61K 47/186* (2013.01); *A61K 47/26* (2013.01)

(58) Field of Classification Search
CPC ...... A61K 31/472; A61K 9/0048; A61K 9/08; A61K 31/5575; A61K 45/06; A61K 47/02; A61K 47/186; A61K 47/26
USPC ........................................................ 514/310
See application file for complete search history.

(56) References Cited

U.S. PATENT DOCUMENTS

| | | | |
|---|---|---|---|
| 4,146,637 A | 3/1979 | Metz et al. |
| 4,337,256 A | 6/1982 | Yasushi et al. |
| 4,456,757 A | 6/1984 | Hidaka et al. |
| 4,709,032 A | 11/1987 | Hidaka et al. |
| 4,911,928 A | 3/1990 | Wallach |
| 4,954,512 A | 9/1990 | Oguro et al. |
| 5,508,288 A | 4/1996 | Forbes et al. |
| 5,519,036 A | 5/1996 | Himmelsbach et al. |
| 5,770,759 A | 1/1998 | Ueno et al. |
| 5,798,380 A | 8/1998 | Kaufman et al. |
| 5,889,052 A | 3/1999 | Klimko et al. |
| 5,891,646 A | 4/1999 | Barak et al. |
| 5,977,173 A | 11/1999 | Wos et al. |
| 5,994,397 A | 11/1999 | Selliah et al. |
| 6,025,392 A | 2/2000 | Selliah et al. |
| 6,030,999 A | 2/2000 | Stjemschantz et al. |
| 6,037,364 A | 3/2000 | Burk |
| 6,037,368 A | 3/2000 | Selliah et al. |
| 6,048,895 A | 4/2000 | Wos et al. |
| 6,110,693 A | 8/2000 | Barak et al. |
| 6,110,912 A | 8/2000 | Kaufman et al. |
| 6,362,177 B1 | 3/2002 | Shiota et al. |
| 6,586,425 B2 | 7/2003 | Kaufman et al. |
| 6,699,891 B1 | 3/2004 | Kawaanishi et al. |
| 6,787,534 B2 | 9/2004 | Haneda |
| 7,268,143 B2 | 9/2007 | Jagtap et al. |
| 7,329,684 B2 | 2/2008 | Mjalli et al. |
| 7,345,158 B2 | 3/2008 | Egashira et al. |
| 7,361,678 B2 | 4/2008 | Mjalli et al. |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,129,411 B2 | 3/2012 | Ehara et al. |
| 8,278,294 B2 | 10/2012 | Plettenburg et al. |
| 8,357,699 B2 | 1/2013 | deLong et al. |
| 8,394,826 B2 | 3/2013 | deLong et al. |

(Continued)

FOREIGN PATENT DOCUMENTS

| | | |
|---|---|---|
| EP | 0109023 | 5/1984 |
| EP | 0232569 | 8/1987 |

(Continued)

OTHER PUBLICATIONS

United States Patent Office Notice of Allowance for U.S. Appl. No. 13/442,263 dated Apr. 15, 2014 (8 pages).

(Continued)

*Primary Examiner* — Yevgeny Valenrod

(74) *Attorney, Agent, or Firm* — K&L Gates LLP; Louis C. Cullman; Benjamin D. Heuberger

(57) ABSTRACT

The present disclosure provides an ophthalmic composition comprising 4-(3-amino-1-(isoquinolin-6-ylamino)-1-oxo-propan-2-yl)benzyl 2,4-dimethylbenzoate or its pharmaceutically acceptable salts; about 0.01% weight/volume to about 1.0% weight/volume of a buffer; and about 0.01% weight/volume to about 10% weight/volume of a tonicity agent.

16 Claims, No Drawings

(56) References Cited

U.S. PATENT DOCUMENTS

| | | | |
|---|---|---|---|
| 8,415,372 B2 | 4/2013 | Yamada et al. |
| 8,450,344 B2 | 5/2013 | deLong et al. |
| 8,455,513 B2 | 6/2013 | deLong et al. |
| 8,455,514 B2 | 6/2013 | deLong et al. |
| 8,455,647 B2 | 6/2013 | deLong et al. |
| 8,716,310 B2 | 5/2014 | deLong et al. |
| 8,759,388 B2 | 7/2014 | deLong et al. |
| 8,809,326 B2 | 8/2014 | Bosanac et al. |
| 8,871,757 B2 | 10/2014 | deLong et al. |
| 8,921,392 B2 | 12/2014 | deLong et al. |
| 9,096,569 B2 | 8/2015 | deLong et al. |
| 9,255,101 B2 | 2/2016 | Berrebi-Bertrand et al. |
| 9,365,518 B2 | 6/2016 | deLong et al. |
| 9,415,043 B2 | 8/2016 | Kopczynski |
| 9,512,101 B2 | 12/2016 | deLong et al. |
| 9,643,927 B1 | 5/2017 | Sturdivant et al. |
| 9,849,122 B2 | 12/2017 | Kopczynski et al. |
| 9,884,840 B2 | 2/2018 | deLong et al. |
| 9,890,123 B2 | 2/2018 | deLong et al. |
| 9,931,336 B2 | 4/2018 | Kopczynski et al. |
| 9,951,059 B2 | 4/2018 | deLong et al. |
| 9,963,432 B2 | 5/2018 | Sturdivant et al. |
| 9,993,470 B2 | 6/2018 | Kopczynski et al. |
| 10,112,920 B2 | 10/2018 | deLong et al. |
| 10,174,017 B2 | 1/2019 | deLong et al. |
| 10,316,029 B2 | 6/2019 | deLong et al. |
| 10,472,327 B2 | 11/2019 | deLong et al. |
| 10,532,993 B2 | 1/2020 | deLong et al. |
| 10,568,878 B2 | 2/2020 | Kopczynski et al. |
| 10,588,901 B2 | 3/2020 | Kopczynski et al. |
| 10,654,844 B2 | 5/2020 | deLong et al. |
| 10,858,339 B2 | 12/2020 | deLong et al. |
| 10,882,840 B2 | 1/2021 | deLong et al. |
| 10,899,714 B2 | 1/2021 | deLong et al. |
| 11,020,385 B2 | 6/2021 | Kopczynski et al. |
| 11,021,456 B2 | 6/2021 | deLong et al. |
| 11,028,081 B2 | 6/2021 | deLong et al. |
| 11,185,538 B2 | 11/2021 | Kopczynski et al. |
| 11,197,853 B2 | 12/2021 | Kopczynski et al. |
| 11,312,700 B2 | 4/2022 | deLong et al. |
| 11,389,441 B2 | 7/2022 | Lin et al. |
| 2004/0091946 A1 | 5/2004 | Oakley et al. |
| 2004/0157859 A1 | 8/2004 | Wu et al. |
| 2004/0176462 A1 | 9/2004 | Kawanishi et al. |
| 2005/0032125 A1 | 2/2005 | Oakley et al. |
| 2005/0054558 A1 | 3/2005 | Benowitz |
| 2005/0176712 A1 | 8/2005 | Wakabayashi et al. |
| 2005/0245509 A1 | 11/2005 | Nakajima et al. |
| 2005/0282805 A1 | 12/2005 | Hangeland et al. |
| 2006/0270670 A1 | 11/2006 | Chew et al. |
| 2007/0111983 A1 | 5/2007 | Fong |
| 2007/0123561 A1 | 5/2007 | Lee et al. |
| 2007/0129404 A1 | 6/2007 | Hagihara et al. |
| 2007/0135499 A1 | 6/2007 | deLong et al. |
| 2007/0149473 A1 | 6/2007 | Chatterton et al. |
| 2007/0149548 A1 | 6/2007 | Hellberg et al. |
| 2007/0167444 A1 | 7/2007 | Kuramochi et al. |
| 2007/0203174 A1 | 8/2007 | Klimko et al. |
| 2007/0238741 A1 | 10/2007 | Nagarathnam et al. |
| 2008/0021026 A1 | 1/2008 | Kahraman et al. |
| 2008/0021217 A1 | 1/2008 | Borchardt |
| 2008/0058384 A1 | 3/2008 | Lee et al. |
| 2008/0096238 A1 | 4/2008 | Sharif et al. |
| 2008/0125427 A1 | 5/2008 | Sehon et al. |
| 2008/0139595 A1 | 6/2008 | Schirok et al. |
| 2008/0153799 A1 | 6/2008 | Laurent et al. |
| 2008/0153813 A1 | 6/2008 | Chen et al. |
| 2008/0161297 A1 | 7/2008 | Bosanac et al. |
| 2008/0194584 A1 | 8/2008 | Birault et al. |
| 2008/0275029 A1 | 11/2008 | Berdini et al. |
| 2008/0287516 A1 | 11/2008 | Wu et al. |
| 2009/0005321 A1 | 1/2009 | Zimmer et al. |
| 2009/0069371 A1 | 3/2009 | deLong et al. |
| 2009/0143381 A1 | 6/2009 | Ruah et al. |
| 2010/0004239 A1 | 1/2010 | Tang et al. |
| 2010/0056568 A1 | 3/2010 | Plettenburg et al. |
| 2010/0063025 A1 | 3/2010 | Plettenburg et al. |
| 2010/0093790 A1 | 4/2010 | deLong et al. |
| 2010/0105650 A1 | 4/2010 | Plettenburg et al. |
| 2011/0015204 A1 | 1/2011 | Bencsik et al. |
| 2011/0039893 A1 | 2/2011 | Kori et al. |
| 2012/0040994 A1 | 2/2012 | Nakajima et al. |
| 2012/0135984 A1 | 5/2012 | deLong et al. |
| 2012/0322871 A1 | 12/2012 | Mercier |
| 2013/0296363 A1 | 11/2013 | Faraoni et al. |
| 2013/0310370 A1 | 11/2013 | Mizuno |
| 2013/0318457 A1 | 11/2013 | Bjorklund |
| 2014/0187617 A1 | 7/2014 | deLong et al. |
| 2014/0275160 A1 | 9/2014 | Kopczynski |
| 2014/0275161 A1* | 9/2014 | Kopczynski ............ A61K 47/55 546/141 |
| 2014/0288086 A1 | 9/2014 | Cui et al. |
| 2014/0357652 A1 | 12/2014 | Bosanac et al. |
| 2015/0175534 A1 | 6/2015 | Harvey et al. |
| 2015/0175549 A1 | 6/2015 | deLong et al. |
| 2015/0266881 A1 | 9/2015 | Tomita et al. |
| 2015/0297581 A1 | 10/2015 | Bosanac et al. |
| 2016/0016951 A1 | 1/2016 | Schiemann et al. |
| 2016/0243102 A1 | 8/2016 | Bosanac et al. |
| 2016/0272589 A1 | 9/2016 | deLong et al. |
| 2017/0000819 A1 | 1/2017 | Capriotti et al. |
| 2019/0322625 A1 | 10/2019 | deLong et al. |
| 2020/0102290 A1 | 4/2020 | deLong et al. |
| 2020/0276179 A1 | 9/2020 | Kopczynski et al. |
| 2021/0253547 A1 | 8/2021 | deLong et al. |
| 2021/0363141 A1 | 11/2021 | deLong et al. |
| 2022/0088000 A1 | 3/2022 | Kopczynski et al. |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |
| JP | 2007236388 | 9/2007 |
| JP | 2007246466 | 9/2007 |
| JP | 2013-35802 A | 2/2013 |
| JP | 2014-19650 A | 2/2014 |
| WO | 1988/003137 A1 | 5/1988 |
| WO | 1993/018028 | 9/1993 |
| WO | 1995/019964 | 7/1995 |
| WO | 1996/010407 | 4/1996 |
| WO | 1997/023223 | 7/1997 |
| WO | 1998/012175 | 3/1998 |
| WO | 1998/020880 | 5/1998 |
| WO | 1998/020881 | 5/1998 |
| WO | 1998/021180 | 5/1998 |
| WO | 1998/021181 | 5/1998 |
| WO | 1998/021182 | 5/1998 |
| WO | 1998/039293 | 9/1998 |
| WO | 1988/050024 | 11/1998 |
| WO | 1998/057930 | 12/1998 |
| WO | 1998/057942 | 12/1998 |
| WO | 1999/002165 | 1/1999 |
| WO | 1999/012895 | 3/1999 |
| WO | 1999/012896 | 3/1999 |
| WO | 1999/012898 | 3/1999 |
| WO | 1999/025358 | 5/1999 |
| WO | 1999/026629 | 6/1999 |
| WO | 1999/032441 | 7/1999 |
| WO | 2000/003736 | 1/2000 |
| WO | 2000/003980 | 1/2000 |
| WO | 2000/071508 | 11/2000 |
| WO | 2000/076970 | 12/2000 |
| WO | 2001/037826 | 5/2001 |
| WO | 2001/047891 | 7/2001 |
| WO | 2001/053268 | 7/2001 |
| WO | 2001/053274 | 7/2001 |
| WO | 2001/056607 | 8/2001 |
| WO | 2002/022576 | 3/2002 |
| WO | 2002/032864 | 4/2002 |
| WO | 2002/085857 | 10/2002 |
| WO | 2002/085859 | 10/2002 |

(56) References Cited

FOREIGN PATENT DOCUMENTS

| WO | 2003/064397 | | 8/2003 |
|---|---|---|---|
| WO | 2003/068749 | | 8/2003 |
| WO | 2003/073999 | | 9/2003 |
| WO | 2003/080578 | | 10/2003 |
| WO | 2004/029045 | | 4/2004 |
| WO | 2004/078747 | | 9/2004 |
| WO | 2005/020921 | | 3/2005 |
| WO | 2005/035503 | | 4/2005 |
| WO | 2005/037257 | | 4/2005 |
| WO | 2006/041119 | | 4/2006 |
| WO | 2006/051290 | | 5/2006 |
| WO | 2006/062982 | | 6/2006 |
| WO | 2006/076706 | | 7/2006 |
| WO | 2007/008926 | | 1/2007 |
| WO | 2007/008942 | | 1/2007 |
| WO | 2007/060028 | | 5/2007 |
| WO | 2007/065916 | | 6/2007 |
| WO | 2007/076360 | | 7/2007 |
| WO | 2007/076367 | | 7/2007 |
| WO | 2007/100880 | | 9/2007 |
| WO | 2007/0142323 | | 12/2007 |
| WO | 2008/011557 | | 1/2008 |
| WO | 2008/011560 | | 1/2008 |
| WO | 2008/016016 | | 2/2008 |
| WO | 2008/036459 | | 3/2008 |
| WO | 2008/036540 | | 3/2008 |
| WO | 2008/049000 | | 4/2008 |
| WO | 2008/049919 | | 5/2008 |
| WO | 2008/054999 | | 5/2008 |
| WO | 2008/077057 | | 6/2008 |
| WO | 2008/077550 | | 7/2008 |
| WO | 2008/077551 | | 7/2008 |
| WO | 2008/077552 | | 7/2008 |
| WO | 2008/077553 | | 7/2008 |
| WO | 2008/077554 | | 7/2008 |
| WO | 2008/077555 | | 7/2008 |
| WO | 2008/077556 | | 7/2008 |
| WO | 2008/079880 | | 7/2008 |
| WO | 2008/079945 | | 7/2008 |
| WO | 2008/086269 | | 7/2008 |
| WO | 2008/124665 | | 10/2008 |
| WO | 2009/091898 | | 7/2009 |
| WO | 2010/011853 | | 1/2010 |
| WO | 2010/019903 | | 2/2010 |
| WO | 2010/126626 | | 11/2010 |
| WO | 2010/127329 | | 11/2010 |
| WO | 2010/127330 | | 11/2010 |
| WO | 2010/146881 | | 12/2010 |
| WO | 2011/085351 | A2 | 7/2011 |
| WO | 2012/063237 | | 5/2012 |
| WO | 2012/105674 | | 8/2012 |
| WO | 2014/144781 | | 9/2014 |
| WO | 2016/123627 | | 8/2016 |
| WO | 2018/034702 | | 2/2018 |
| WO | 2018/045091 | | 3/2018 |
| WO | 2018/183911 | A1 | 10/2018 |
| WO | 2019/191654 | A1 | 10/2019 |
| WO | 2020/056345 | A1 | 3/2020 |

OTHER PUBLICATIONS

United States Patent Office Action for U.S. Appl. No. 13/442,263 dated Dec. 19, 2012 (13 pages).
European Search Report for European Patent Application No. 18206195.2 dated Feb. 11, 2019 (10 pages).
United States Patent Office Action for U.S. Appl. No. 13/442,263 dated Jun. 12, 2013 (17 pages).
United States Patent Office Notice of Allowance for U.S. Appl. No. 13/723,811 dated Aug. 19, 2014 (11 pages).
United States Patent Office Notice of Allowance for U.S. Appl. No. 13/768,594 dated Oct. 29, 2013 (7 pages).
United States Patent Office Notice of Allowance for U.S. Appl. No. 14/213,961 dated Jun. 20, 2016 (8 pages).
United States Patent Office Notice of Allowance for U.S. Appl. No. 14/273,895 dated Apr. 1, 2015 (8 pages).
United States Patent Office Notice of Allowance for U.S. Appl. No. 14/583,439 dated Feb. 12, 2016 (8 pages).
United States Patent Office Notice of Allowance for U.S. Appl. No. 14/790,376 dated Aug. 2, 2016 and supplemental Notice of Allowability dated Aug. 19, 2016 (10 pages).
Yamashita et al., "The therapeutic effects of Rho-Rock inhibitors on CNS disorder," Therapeutics and Clinical Risk Management, 2008, vol. 4, pp. 605-615.
International Search Report and Written Opinion dated Aug. 23, 2018 for International Application No. PCT/US2018/025494 filed on Mar. 30, 2018.
Westra et al., "p38 Mitogen-Activated Protein Kinase (MAPK) in Rheumatoid Arthritis." Mini-Reviews in Medicinal Chemistry (2006) 6(8):867-874.
Westaway et al., "N-tetrahydroquinolinyl, N-quinolinyl and N-isoquinolinyl biaryl carboxamides as antagonists of TRPV1." Biorg. Med. Chem. Lett. (2006) 16:4533-4536.
Van Muijl Wijk-Koezen et al., "A novel class of adenosine A3 receptor-ligands. 2. Structure affinity profile of a series of isoquinoline and quinazoline compounds." J. Med. Chem. (1998) 41:3994-4000.
Vippagunta et al., "Cystalline solids." Advanced Drug Delivery Reviews, 48:3-26 (2001).
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
International Search Report and Written Opinion dated Nov. 15, 2019, for International Patent Application Serial No. PCT/US2019/051136 filed on Sep. 13, 2019.
Donegan et al., Discovery of molecular therapeutics for glaucoma: Challenges, successes, and promising directions. Journal of Medicinal Chemistry, vol. 59, Issue 3, pp. 788-809 (2016).
International Search Report and Written Opinion dated Jul. 25, 2019, for International Patent Application Serial No. PCT/US2019/024954 filed on Mar. 29, 2019.
Bhatia et al., A review on Bioisosterism: A Rational approach for drug design and molecular modification. Pharmacologyonline, 1:272-299 (2011).
Gould, Philip L., Salt selection for basic drugs. International Journal of Pharmaceutics, vol. 33, pp. 201-217 (1986).
Williams et al., Ocular hypotensive effect of the Rho kinase inhibitor AR-12286 in patients with glaucoma and ocular hypertension. Am. J. Ophthalmol., vol. 152, pp. 834-841 (2011).
Yingling et al., ARVO Annual Meeting Abstract, Apr. 2009, IOP-Lowering Efficacy and Tolerability of AR-12286, a Potent Kinase Inhibitor for the Treatment of Glaucoma. Investigative Ophthalmology & Visual Science, Apr. 2009, vol. 50, 4063 (2009).
Rowe et al., Boric Acid. Handbook of Pharmaceutical Excipients, Fifth Edition (2006). Pharmaceutical Press and American Pharmacists Association.
Elder et al., Review: The utility of sulfonate salts in drug development. Journal of Pharmaceutical Sciences, 99 (7):2948-2961 (2010).
U.S. Appl. No. 17/841,433, filed Jun. 15, 2022.
U.S. Appl. No. 17/722,832, filed Apr. 18, 2022.
Extended European Search Report, dated Apr. 30, 2021, for European Patent Application Serial No. 20203979.8.
Salt selection in drug development. PharmTech.com (2008) accessed May 6, 2020.
Extended European Search Report, dated Mar. 29, 2021, for European Patent Application Serial No. 20207657.6.
United States Patent Notice of Allowability for U.S. Appl. No. 11/621,887 dated Oct. 29, 2010 (14 pages).
United States Patent Office Action for U.S. Appl. No. 11/856,740 dated Aug. 16, 2013 (14 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).

(56) References Cited

OTHER PUBLICATIONS

United States Notice of Allowance for U.S. Appl. No. 12/009,326 dated Feb. 3, 2011 (8 pages).
United States Patent Office Action for U.S. Appl. No. 12/180,259 dated Jul. 5, 2011 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 12/694,965 dated May 17, 2012 (13 pages).
United States Patent Office Action for U.S. Appl. No. 12/701,963 dated May 10, 2011 (3 pages).
United States Patent Office Action for U.S. Appl. No. 12/704,822 dated Apr. 30, 2012 (34 pages).
United States Patent Office Action for U.S. Appl. No. 12/704,822 dated May 8, 2014 (13 pages).
United States Patent Office Action for U.S. Appl. No. 12/704,822 dated Oct. 10, 2013 (11 pages).
United States Patent Office Action for U.S. Appl. No. 13/017,708 dated Apr. 3, 2012 (11 pages).
United States Patent Office Action for U.S. Appl. No. 13/230,105 dated Mar. 5, 2012 (8 pages).
United States Patent Office Action for U.S. Appl. No. 13/318,457 dated Jun. 6, 2013 (12 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Action for U.S. Appl. No. 13/768,594 dated Jul. 10, 2013 (14 pages).
United States Patent Office Action for U.S. Appl. No. 14/138,592 dated Dec. 9, 2014 (14 pages).
United States Patent Office Action for U.S. Appl. No. 14/138,592 dated Jul. 28, 2014 (17 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Action for U.S. Appl. No. 14/461,597 dated Jan. 30, 2015 (19 pages).
United States Patent Office Action for U.S. Appl. No. 14/583,439 dated Jun. 23, 2015 (6 pages).
United States Patent Office Action for U.S. Appl. No. 14/583,439 dated Oct. 30, 2015 (7 pages).
United States Patent Office Action for U.S. Appl. No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/790,376 dated Jan. 22, 2016 (14 pages).
United States Patent Office Action for U.S. Appl. No. 15/076,216 dated Sep. 1, 2016 (6 pages).
United States Patent Office Advisory Action for U.S. Appl. No. 11/856,740 dated Feb. 10, 2011 (3 pages).
United States Patent Office Final Rejection for U.S. Appl. No. 12/704,822 dated Jan. 16, 2013 (16 pages).
United States Patent Office Final Rejection for U.S. Appl. No. 13/230,105 dated Jul. 9, 2012 (11 pages).
United States Patent Office Final Rejection for U.S. Appl. No. 13/318,457 dated Nov. 27, 2013 (13 pages).
United States Patent Office Final Rejection for U.S. Appl. No. 13/442,263 dated Dec. 6, 2013 (8 pages).
United States Patent Office Notice of Allowability for U.S. Appl. No. 13/017,708 dated Dec. 12, 2012 (5 pages).
United States Patent Office Notice of Allowance for U.S. Appl. No. 11/621,887 dated Feb. 27, 2013 (8 pages).
United States Patent Office Notice of Allowance for U.S. Appl. No. 11/856,740 dated Apr. 1, 2014 (8 pages).
United States Patent Office Notice of Allowance for U.S. Appl. No. 12/009,326 dated Feb. 25, 2013 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/180,259 dated Dec. 19, 2011 (6 pages).
United States Patent Office Notice of Allowance for U.S. Appl. No. 12/180,259 dated Feb. 25, 2013 (8 pages).
United States Patent Office Notice of Allowance for U.S. Appl. No. 12/694,965 dated Nov. 19, 2012 (4 pages).
United States Patent Office Notice of Allowance for U.S. Appl. No. 12/694,965 dated Nov. 2, 2012 (8 pages).
United States Patent Office Notice of Allowance for U.S. Appl. No. 12/704,822 dated Sep. 9, 2014 (11 pages).
United States Patent Office Notice of Allowance for U.S. Appl. No. 13/017,708 dated Oct. 23, 2012 (7 pages).
United States Patent Office Notice of Allowance for U.S. Appl. No. 13/017,708 dated Sep. 17, 2012 (8 pages).
United States Patent Office Notice of Allowance for U.S. Appl. No. 13/230,105 dated Mar. 19, 2013 (5 pages).
Berge et al, 1977, "Pharmaceutically Acceptable Salts." J. Pharm. Sci. vol. 66, pp. 1-19.
Bird, G.J. et al., "N-methyl as a bioisostere for the oxygen link between the aromatic rings of aryloxyphenoxypropionate herbicides," Bioorg. Med. Chem. Lett. (1997) 7:1489-1492.
Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18):4029-37.
C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.
Calmes et al., Asymmetric Synthesis of (S)-beta^2-Homoarylglycines. Eur. J. Org. Chem. 2000, 2459-2466.
Canadian Patent Office Action for Application No. 2,731,869 dated Jun. 9, 2015 (3 pages).
Canadian Patent Office Action for Application No. 2,731,869 dated Feb. 18, 2016 (4 pages).
Canadian Patent Office Action for Application No. 2,760,562 dated Feb. 2, 2015 (4 pages).
Canadian Patent Office Action for Application No. 2,760,562 dated Jul. 3, 2015 (3 pages).
Canadian Patent Office Action for Application No. 2,712,443 dated Dec. 27, 2013 (3 pages).
Capdeville, R. et al., "Glivec (STI571, IMATINIB), A Rationally Developed, Targeted Anticancer Drug", Nature Reviews Drug Discovery (2002) 1:493-502.
Chen, P. et al., "Identification of novel and potent isoquinoline aminooxazole-based IMPDH inhibitors," Bioorg. Med. Chem. Lett. (2003) 13(7):1345-1348.
Cheung et al., N-methylamino acids in peptide synthesis. V. The syntesis of N-tert-butyloxycarbonyl, N-methylamino acids by N-methylation. Can. J. Chem. 1977, 55,906-910.
International Search Report and Written Opinion for International Application No. PCT/US2017/025609 dated Jul. 3, 2017 (8 pages).
International Search Report and Written Opinion for International Application No. PCT/US2017/065631 dated Feb. 13, 2018 (6 pages).
Ito, N. et al., "A medium-term rat liver bioassay for rapid in vivo detection of carcinogenic potential of chemicals," Cancer Science, Jan. 2003, vol. 94, No. 1, pp. 3-8.
Jacobs, M. et al., "The structure of dimeric ROCK I reveals the mechanism for ligand selectivity," J. Bio. Chem., 2006, pp. 260-268, published on Jan. 6, 2006.
Japanese Patent Office Action for Application No. 2009-545622 dated Mar. 1, 2013 (8 pages—including English Translation).

(56) References Cited

OTHER PUBLICATIONS

Japanese Patent Office Action for Application No. 2009-545622 dated Oct. 21, 2013 (8 pages—Including English Translation).
Japanese Patent Office Action for Application No. 2010-543237 dated Aug. 8, 2013 (10 pages—Including English Translation).
Japanese Patent Office Action for Application No. 2010-543237 dated Jan. 8, 2014 (2 pages—Including English Translation).
Japanese Patent Office Action for Application No. 2011-520203 dated Jan. 28, 2014 (8 pages, English translation included).
Japanese Patent Office Action for Application No. 2012-508492 dated Apr. 2, 2015 (4 pages, English translation included).
Japanese Patent Office Action for Application No. 2012-508492 dated Apr. 7, 2014 (5 pages, English translation only).
Japanese Patent Office Action for Application No. 2014-131231 dated Jan. 14, 2015 (8 pages, English translation attached).
Japanese Patent Office Action for Application No. 2014-131231 dated Jan. 27, 2016 (3 pages, English translation only).
Japanese Patent Office Action for Application No. 2015-216395 dated Nov. 14, 2016 (7 pages including translation).
Karaman, M.W. et al., "A quantitative analysis of kinase inhibitor selectivity," Nature Biotech. (2008) 26(1):127-132.
Katritzky, A.R. et al., "Benzotriazole mediated amino-, amide-, alkoxy- and alkylthio-alkylation," Tetrahedron (2005) 61:2555-2581.
Kumar et al., Catalyst-free water mediated reduction of nitroarenes using glucose as a hydrogen source. RSC Advances, 3:4894-4898 (2013).
Lala, P.K. et al., "Role of nitric oxide in tumor progression: lessons from experimental tumors," Cancer and Metastasis Reviews (1998) 17:91-106.
Liljebris, C. et al., "Derivatives of 17-Pheny 1-18,19,20-trinorprostaglandin F2a Isopropyl Ester: Antiglaucoma Agents," J. Med. Chem. (1995) 38(2):289-304.
Loge et al., Synthesis and pharmacological study of rho-kinase inhibitors: Pharmacomodulations on the lead compound Fasudil. J. of Enzy Inhib & Med Chem, 2003,18(2),127-128.
Matsui et al., "Novel 5-HT3 antagonists. Isoquinolinones and 3-aryl-2-pyridones." J. Med. Chem. (1992) 35:3307-3319.
McCutcheon's, "Emulsifiers & Detergents", North American Edition (1994) vol. 1:236-239.
Meanwell, "Synopsis of some recent tactocal application of bioisosteres in drug design," J. Med. Chem., 2011, vol. 54, pp. 2529-2591.
Nakanishi et al., Effects of protein kinase inhibitors and protein phosphatase inhibitors on cyclic AMP-dependent down-regulation of vesicular monoamine transport in pheochromocytoma PC12 cells. FEBS Letters 368, (1995) 411-414.
Oakley et al., "The Cellular Distribution of Fluorescently Labeled Arrestins Provides a Robust, Sensitive and Universal Assay for Screening G Protein-Coupled Receptors." Assay and Drug Development Technologies vol. 1, No. 1-1:21-30 (2002).
Olson, "Application for ROCK kinase inhibition," Current Opinion in Cell Biology, 2008, vol. 20, pp. 242-248.
Parang et al., "Design strategies for protein kinase inhibitors." Curr. Opin. In Drug Disc. & Dev. (2004) 7(5):617-629.
Pardridge, "The Blood-Brain Barrier: Bottleneck in Brain Drug development," J. Am. Soc. Exper. NeuroTherapeutics, 2005, vol. 2, p. 3-14.
Partial International Search Report and Invitation to pay Additional Fees for Application No. PCT/US2009/031117 dated Apr. 16, 2009 (4 pages).
Penmetsa et al., Development of Reversed-Phase Chiral HPLC Methods Using Mass Spectrometry Compatible Mobile Phases. J. Liquid Chroma. & Rel. Tech. 23(6):831-839 (2000).
Penn et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. 288(2):428-437 (1999).
Pharmasolve (N-Methyl-2-Pyrrolidone) product spcification, International Specialty Products, 2000, 10 pages.
Poradowska et al., The Preparation of 6-Aminoisoquinoline. Synthesis 11:733, 1975.
PubChem, AC1 NQAJU (compound sumary for CID 5172372) '372' date created: Sep. 26, 2005 date access: Jan. 5, 2016, 10 pages.
Rashid et al., "Development of Rho-kinase inhibitors for cardiovascular medicine," Trends in Pharmacological Science, 2007, vol. 28, pp. 296-302.
Shankar et al., "Protein-kinase-specific inhibitors block Langerhans' cell migration by inhibiting interleukin-1alpha release." Immunology (1999) 96:230-235.
Sharma et al., Highly Chemo- and Regioselective Reduction of Aromatic Nitro Compounds Catalyzed by Recyclable Copper(II) as well as Cobalt(II) Phthalocyanines. Advanced Synthesis and Catalysis, 352:1834-1840 (2010).
Sharma et al., Zinc phthalocyanine with PEG-400 as a recyclable catalytic system for selective reduction of aromatic nitro compounds. Green Chem., 14:2289-2293 (2012).
Sharma et al., Phosphane-Free Green Protocol for Selective Nitro Reduction with an Iron-Based Catalyst. Chem. Eur. J., 17:5903-5907 (2011).
Stirewalt et al., "The Role of FLT3 In Haematopoietic Malignancies." Nature Reviews Cancer (2003) 3:650-665.
STN Registry Database entry for CAS RN 309930-43-6, Published in database Dec. 20, 2000.
Sturdivant et al., Discovery of the ROCK inhibitor netarsudil for the treatment of open-angle glaucoma. Bioorganic & Medicinal Chemistry Letters, 26:2475-2480 (2016).
Sturdivant et al., Identification of intermediates in the stepwise reduction of 1,3-dichloro-6nitroisoquinoline to 6-aminoisiquinoline. 248th National Meeting of the American Chemical Society, Aug. 2014, MEDI 153.
Tamura, M., et al., "Development of specific Rho-kinase inhibitors and their clinical application," Biochimica et Biophysica Acta, 2005, vol. 1754, pp. 245-252.
Torres, G.E. et al. (2003). "Plasma membrane monoamine transporters: structure, regulation and function". Nat. Rev. Neurosci. 4 (1): 13-25.
United States Office Action for U.S. Appl. No. 11/485,182 dated Apr. 16, 2009 (13 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Office Action for U.S. Appl. No. 12/274,887 dated Jun. 16, 2009 (11 pages).
United States Patent Office Action for U.S. Appl. No. 11/621,887 dated May 18, 2010 (8 pages).
"Cancer", MedlinePlus (retrieved Jul. 6, 2007) 10 pages, http://www.nlm.nih.gov/medlineplus/cancer.html.
Anonymous, "Aerie Pharmaceuticals, Inc. Gets Good News on Glaucoma Treatment" (Feb. 11, 2012) Retrieved from the Internet: URL:http://www.biospace.com.
Australian Patent Examination Report No. 1 for Application No. 2009206075 dated Jan. 29, 2013 (3 pages).
Australian Patent Examination Report for Application No. 2016201754 dated Oct. 19, 2016 (4 pages).
Australian Patent Examination Report No. 1 for Application No. 2010241996 dated Apr. 1, 2015 (4 pages).
Australian Patent Office Action for Application No. 2010241996 dated Mar. 21, 2016 (3 pages).
Banker, G.S. et al., Modern Pharmaceutics, Marcel Dekker, Inc., New York, (1979) Chapters 9 and 10.
Basu et al., Ultrasound-promoted highly efficient reduction of aromatic nitro compounds to the aromatic amines by samarium/ammonium chloride. Tetrahedron Letters, 41:5603-5606 (2000).
Chinese Patent Office Action for Application No. 201480027763.3 dated Nov. 1, 2016 (18 pages including translation).
Dancey, J. et al., "Issues and Progress with Protein Kinase Inhibitors for Cancer Treatment", Nature Reviews Drug Discovery (2003) 2:296-313.
DeLong et al., "Discovery and SAR of a Class of Oculary-active Compounds Displaying a Dual Mechanism of Activity for the

(56) References Cited

OTHER PUBLICATIONS

Treatment of Glaucoma" (May 6-10, 2012) Retrieved from the Internet:URL:http://www.aeriepharma.com.
Dorwald, F.Z., Side Reactions in Organic Synthesis. A Guide to Successful Synthesis Design, Wiley-VCH, Weinheim (2005) IX of Preface and 1-15.
Dowton et al., "Influence of Liposomal Composition on Topical Delivery of Encapsulated Cyclosporin A", S.T.P. Pharma Sciences, vol. 3, pp. 404-407 (1993).
Ehara et al., Structure-based design of substituted piperidines as a new class of highly efficacious oral direct renin inhibitors. ACS Medicinal Chemistry Letters, 5(7):787-792 (2014).
Ehara, abstract only, CA 161:93707 (2014).
European Patent Office Action for Application No. 08713603.2 dated Aug. 14, 2012 (3 pages).
European Patent Office Action for Application No. 08713603.2 dated Nov. 21, 2013 (4 pages).
European Patent Office Action for Application No. 09702189.3 dated Feb. 1, 2011 (5 pages).
European Patent Office Action for Application No. 09702189.3 dated Dec. 28, 2011 (5 pages).
European Patent Office Action for Application No. 09790775.2 dated Oct. 24, 2011 (5 pages).
European Patent Office Search Report for Application No. 15002893.4 dated Jun. 27, 2016 (5 pages).
Extended European Search Report for European Patent Application No. 12007093.3 dated Nov. 23, 2012 (5 pages).
European Patent Office Action for Application No. 12007093.3 dated Mar. 26, 2014 (4 pages).
European Patent Office Action for Application No. 12007093.3 dated Aug. 23, 2013 (5 pages).
European Patent Office Action for Application No. 12007092.5 dated Nov. 23, 2012 (5 pages).
Extended European Search Report for European Patent Application No. 12007089.1 dated Nov. 23, 2012 (5 pages).
European Search Report for European Application No. 18160338.2 dated May 25, 2018 (6 pages).
Examination Report from the Australian Patent Office for Application No. 2008205047 dated Nov. 26, 2012 (6 pages).
Examination Report from the Australian Patent Office for Application No. 2009273932 dated Mar. 13, 2013 (3 pages).
Examination Report from the Australian Patent Office for Application No. 2009273932 dated Jun. 6, 2014 (2 pages).
Fox et al., 19F and 13C GIAO-NMR chemical shifts for the identification of perfluoro-quinoline and -isoquinoline derivatives. Journal of Fluorine Chemistry, 155, pp. 62-71 (2013).
Foye, Foye's Principles of Medicinal Chemistry, 5th Edition (2002) Lippencott, Williams, Wilkins, p. 59-63.
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Golub, T.R. et al., "Molecular classification of cancer: class discovery and class prediction by gene expression monitoring," Science (1999) 286:531-537.
Guha et al., Solid supported rhodium(0) nanoparticles: an efficient catalyst for chemo- and regio-selective transfer hydrogenation of nitroarenes to anilines under microwave irradiation. Tetradedron Letters, 55:2912-2916 (2014).
Hackam, A.S. et al., "The Wnt Signaling Pathway in Retinal Degenerations", IUBMB Life (2005) 57(6):381-388.
Hazeldine, S.T. et al., "II Synthesis and biological evaluation of some bioisosteres and cogeners of the anti tumour agent, 2{ 4[7-chloro-2-quinoxalinyl)oxy ]phenoxy }propionic acid (XK469)," J. Med. Chem. (2002) 45:3130-3137.
He et al., "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9 (2005).

Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Helzner, "Bright New Ideas in Glaucoma Treatment" (2013) Retrieved from the Internet: URL:http://mydigimag.rrd.com. [Ophthalmology Management, vol. 17, Issue: Jan. 2013, pp. 54-56].
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2 Cyclopropanedicarboxylic Acid and TRANS-2-Phenylcyclopropanecarboxylic Acid", Int'l. J. Org. Chem. (1964) 20(5):1695-1699.
International Search Report and Written Opinion for Application No. PCT/US2015/61177 dated Feb. 2, 2016 (16 pages).
International Preliminary Examination Report for Application No. PCT/US2006/026947 dated Jan. 24, 2008 (10 pages).
International Preliminary Report on Patentability for Application No. PCT/US08/50374 dated Jul. 14, 2009 (12 pages).
International Search Report and Written Opinion for Application No. PCT/US2006/026976 dated Feb. 15, 2007 (14 pages).
International Search Report and Written Opinion for Application No. PCT/US2007/078343 dated Apr. 15, 2008 (12 pages).
International Search Report and Written Opinion for Application No. PCT/US2009/031117 dated Sep. 24, 2009 (13 pages).
International Search Report and Written Opinion for Application No. PCT/US2009/051569 dated May 20, 2010 (11 pages).
International Search Report and Written Opinion for Application No. PCT/US2010/022246 dated Nov. 10, 2010 (7 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2014/029335, dated Jul. 2, 2014 (11 pages).
Al-Rashida et al., Diarylsulfonamides and their bioisosteres as dual inhibitors of alkaline phosphatase and carbonic anhydrase: Structure activity/relationship and molecular modelling studies. Bioorganic & Medicinial Chemistry, vol. 23, Issue 10, pp. 2435-2444 (2015).
International Search Report for Application No. PCT/US08/50374 dated Oct. 28, 2008 (7 pages).
International Search Report for Application No. PCT/US2006/026947 dated Nov. 17, 2006 (4 pages).
Invitation to Pay Additional Fees and Partial International Search Report for International Application No. PCT/US2009/051569 dated Oct. 15, 2009 (4 pages).
International Search Report and Written Opinion for International Application No. PCT/US2017/049473 dated Nov. 30, 2017 (15 pages).
Announcement, "Aerie Pharmaceuticals, Inc. Announces Positive Phase 2a Clinical Results for a Fixed Combination of its Rho Kinase Inhibitor, AR-12286, with Travoprost for the Treatment of Glaucoma" (Nov. 1, 2012) Retrieved from the Internet: URL:http://www.biospace.com.
Announcement, "Aerie Pharmaceuticals Announces Positive Phase 2a Clinical Results for its Novel, Dual Mechanism, AR-13324, for the Treatment of Glaucoma" (Nov. 1, 2012).
Bito et al., Textbook excerpt, The ocular effects of prostaglandin and other eicosanoids. New York, Progress in clinical and biological research (cover, content, abstract, p. 329, 343, 344) (1989).
Colligris et al., Potential role of Rho-associated protein kinase inhibitors for glaucoma treatment. Recent Patents on Endocrine, Metabolic & Immune Drug Discovery, 6:89-98 (2012).
Fogagnolo et al., Medical treatment of glaucoma: present and future. Expert Opinion on Investigational Drugs, 20 (7):947-959 (2011).
Gennaro, Alfons, R. Remington's Pharmaceutical Sciences, 1985, 17th Edition, pp. 1418-1419.
Hahmann et al., Rho-kinase inhibitors as therapeutics: from pan inhibition to isoform selectivity. Cell. Mol. Life Sci., 67:171-177 (2010).

(56) References Cited

OTHER PUBLICATIONS

Handbook of Pharmaceutical Salts, Editors: P. Heinrich Stahl and Camille G. Wermuth, Introduction Chapter, pp. 1-7 (2002).
Mizuno et al., Ocular hypotensive mechanism of K-115, a rho-kinase inhibitor, and rho-kinase expression in the eye. ARVO Annual Meeting Abstract, Apr. 2011, Investigative Ophthalmology & Visual Science, vol. 52, 237 (2011).
Paulekuhn et al., Trends in active pharmaceutical ingredient salt selection based on analysis of the Orange Book database. J. Med. Chem., 50:6665-6672 (2007).
Press Release, Kowa Company Ltd., Kowa Announces the Efficacy and Safety of a Novel Rho Kinase Inhibitor (K-115) in the Treatment of Glaucoma, May 9, 2011. The Association for Research in Vision and Ophthalmology (ARVO) 2011.
Song et al., Fasudil, a Rho-associated protein kinase inhibitor, attenuates retinal ischemia and reperfusion injury in rats. International Journal of Molecular Medicine, 28:193-198 (2011).
Yu et al., Mechanisms, Clinical Profile and Role of Prostaglandin and Prostamide Analogues in Antiglaucomatous Therapy. English Abstract. Published Online Jan. 2013, 230:127-132 (2013).
Amano et al., Rho-kinase/ROCK: A key regulator of the cytoskeleton and cell polarity. Cytoskeleton, 67:545-554 (2010).

\* cited by examiner

OPHTHALMIC COMPOSITIONS

RELATED APPLICATIONS

This application is a continuation of U.S. patent application Ser. No. 17/841,433, filed Jun. 15, 2022, which is a continuation of U.S. patent application Ser. No. 15/691,607, filed Aug. 30, 2017, which claims priority of U.S. Provisional Patent Application No. 62/382,237, filed Aug. 31, 2016, the entire content of each of which is incorporated herein by reference.

INTRODUCTION

Ophthalmic compositions are needed which provide sufficient solubility for the active pharmaceutical ingredient, while maintaining stability of the active pharmaceutical ingredient and reducing discomfort upon administration. Typically ophthalmic compositions are administered at or near physiological pH for both ease of dosing and reduced discomfort upon administration. However, not all active pharmaceutical ingredients are sufficiently soluble at physiological pH. Therefore, a composition that both allows for sufficient solubility of the active pharmaceutical ingredient and minimizes discomfort upon administration is needed.

DETAILED DESCRIPTION

In an aspect, the present disclosure provides an ophthalmic composition comprising 4-(3-amino-1-(isoquinolin-6-ylamino)-1-oxopropan-2-yl)benzyl 2,4-dimethylbenzoate or its pharmaceutically acceptable salts; about 0.01% weight/volume to about 1.0% weight/volume of a buffer; and about 0.01% weight/volume to about 10% weight/volume of a tonicity agent.

In another aspect, the present disclosure provides an ophthalmic composition comprising 4-(3-amino-1-(isoquinolin-6-ylamino)-1-oxopropan-2-yl)benzyl 2,4-dimethylbenzoate or its pharmaceutically acceptable salts; boric acid; and mannitol, wherein the composition has a pH from about 4.5 to about 5.2.

In another aspect, the present disclosure provides an ophthalmic composition comprising about 0.02% weight/volume of 4-(3-amino-1-(isoquinolin-6-ylamino)-1-oxopropan-2-yl)benzyl 2,4-dimethylbenzoate or its pharmaceutically acceptable salt; about 4.7% weight/volume of mannitol; about 0.05% weight/volume of boric acid; and about 0.015% weight/volume of benzalkonium chloride; wherein the composition has a pH from about 4.5 to about 5.2.

In another aspect, the present disclosure provides an ophthalmic composition, comprising 4-(3-amino-1-(isoquinolin-6-ylamino)-1-oxopropan-2-yl)benzyl 2,4-dimethylbenzoate or its pharmaceutically acceptable salts; boric acid; mannitol; and latanoprost.

In another aspect, the present disclosure provides methods of treating an ophthalmic disease, the method comprising topically administering to the eye of a patient in need an ophthalmic composition as described herein.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITIONS

In an aspect, the present disclosure provides an ophthalmic composition comprising netarsudil or its pharmaceutically acceptable salts; about 0.01% weight/volume to about 1.0% weight/volume of a buffer; and about 0.01% weight/volume to about 10% weight/volume of a tonicity agent.

a. 4-(3-amino-1-(isoquinolin-6-ylamino)-1-oxopropan-2-yl)benzyl 2,4-dimethylbenzoate In another aspect, provided herein are ophthalmic compositions, comprising: 4-(3-amino-1-(isoquinolin-6-ylamino)-1-oxopropan-2-yl)benzyl 2,4-dimethylbenzoate or a pharmaceutically acceptable salt thereof; about 0.01% weight/volume to about 1.0% weight/volume of a buffer; and about 0.01% weight/volume to about 10% weight/volume of a tonicity agent.

In another aspect, provided herein are ophthalmic compositions, comprising: (S)-4-(3-amino-1-(isoquinolin-6-ylamino)-1-oxopropan-2-yl)benzyl 2,4-dimethylbenzoate or a pharmaceutically acceptable salt thereof; boric acid; and mannitol; wherein the composition has a pH from about 4.5 to about 5.2.

In another aspect, provided herein are ophthalmic compositions, comprising: about 0.02% to about 0.03% weight/volume of (S)-4-(3-amino-1-(isoquinolin-6-ylamino)-1-oxopropan-2-yl)benzyl 2,4-dimethylbenzoate or a pharmaceutically acceptable salt thereof; about 4.7% weight/volume of mannitol; about 0.05% weight/volume of boric acid; and about 0.015% weight/volume of benzalkonium chloride; wherein the composition has a pH from about 4.5 to about 5.2.

In another aspect, provided herein are ophthalmic compositions, comprising: (S)-4-(3-amino-1-(isoquinolin-6-ylamino)-1-oxopropan-2-yl)benzyl 2,4-dimethylbenzoate or a pharmaceutically acceptable salt thereof; boric acid; mannitol; and latanoprost.

In another aspect, provided herein are ophthalmic compositions, comprising: mixture of (S)-4-(3-amino-1-(isoquinolin-6-ylamino)-1-oxopropan-2-yl)benzyl 2,4-dimethylbenzoate or a pharmaceutically acceptable salt thereof and (R)-4-(3-amino-1-(isoquinolin-6-ylamino)-1-oxopropan-2-yl)benzyl 2,4-dimethylbenzoate or a pharmaceutically acceptable salt thereof; boric acid; and mannitol; wherein the composition has a pH from about 4.5 to about 5.2.

In another aspect, provided herein are ophthalmic compositions, comprising: about 0.02% to about 0.03% weight/volume of a mixture of (S)-4-(3-amino-1-(isoquinolin-6-ylamino)-1-oxopropan-2-yl)benzyl 2,4-dimethylbenzoate or a pharmaceutically acceptable salt thereof and (R)-4-(3-amino-1-(isoquinolin-6-ylamino)-1-oxopropan-2-yl)benzyl 2,4-dimethylbenzoate or a pharmaceutically acceptable salt thereof; about 4.7% weight/volume of mannitol; about 0.05% weight/volume of boric acid; and about 0.015% weight/volume of benzalkonium chloride; wherein the composition has a pH from about 4.5 to about 5.2.

In another aspect, provided herein are ophthalmic compositions, comprising: a mixture of (S)-4-(3-amino-1-(isoquinolin-6-ylamino)-1-oxopropan-2-yl)benzyl 2,4-dimethylbenzoate or a pharmaceutically acceptable salt thereof and (R)-4-(3-amino-1-(isoquinolin-6-ylamino)-1-oxopropan-2-yl)benzyl 2,4-dimethylbenzoate or a pharmaceutically acceptable salt thereof; boric acid; mannitol; and latanoprost.

In some embodiments of the compositions provided herein, the pH is from about 3.5 to about 5.5.

In some embodiments of the compositions provided herein, the pH is from about 4.5 to about 5.2.

In some embodiments, the compositions further comprise a preservative.

In some embodiments, the preservative comprises benzalkonium chloride.

In some embodiments, the compositions further comprise an emulsifying agent.

In some embodiments, the emulsifying agent comprises polyoxyl 40 stearate, polyethoxylated castor oil, or a combination thereof.

In some embodiments, the tonicity agent comprises mannitol.

In some embodiments, the buffer comprises boric acid or its salts.

In some embodiments, the compositions further comprise water.

In some embodiments, the compositions further comprise a pH adjusting agent.

In some embodiments, the 4-(3-amino-1-(isoquinolin-6-ylamino)-1-oxopropan-2-yl)benzyl 2,4-dimethylbenzoate is a dimesylate salt.

In some embodiments, the 4-(3-amino-1-(isoquinolin-6-ylamino)-1-oxopropan-2-yl)benzyl 2,4-dimethylbenzoate or a pharmaceutically acceptable salt thereof is (S)-4-(3-amino-1-(isoquinolin-6-ylamino)-1-oxopropan-2-yl)benzyl 2,4-dimethylbenzoate or a pharmaceutically acceptable salt thereof.

In some embodiments, the compositions further comprise a second ophthalmic active compound.

In some embodiments, the second ophthalmic active compound is a prostaglandin analog.

In some embodiments, the prostaglandin analog is latanoprost or travoprost.

In some embodiments, the compositions comprise about 0.02% w/v to about 0.03% w/v of 4-(3-amino-1-(isoquinolin-6-ylamino)-1-oxopropan-2-yl)benzyl 2,4-dimethylbenzoate or a pharmaceutically acceptable salt thereof.

In some embodiments, the compositions comprise about 4.7% weight/volume of mannitol.

In some embodiments, the compositions comprise about 0.05% weight/volume of boric acid.

In some embodiments, the compositions comprise about 0.015% weight/volume of benzalkonium chloride.

In some embodiments, the compositions further comprise 0.005% weight/volume of latanoprost or travoprost.

In some embodiments, the pharmaceutically acceptable salt is the dimesylate salt.

In some embodiments, the pharmaceutically acceptable salt is the dihydrochloride salt.

In some embodiments, the pharmaceutically acceptable salt is the mesylate salt.

In some embodiments, the pharmaceutically acceptable salt is the hydrochloride salt.

4-(3-Amino-1-(isoquinolin-6-ylamino)-1-oxopropan-2-yl)benzyl 2,4-dimethylbenzoate or its pharmaceutically acceptable salts may be present in the ophthalmic composition in an amount of about 0.01% w/v to about 0.06% w/v. Suitably, 4-(3-amino-1-(isoquinolin-6-ylamino)-1-oxopropan-2-yl)benzyl 2,4-dimethylbenzoate or its pharmaceutically acceptable salts may be present in an amount of about 0.02% w/v to about 0.03% w/v, depending on the particular salt form. For example, 0.0285% w/v of 4-(3-amino-1-(isoquinolin-6-ylamino)-1-oxopropan-2-yl)benzyl 2,4-dimethylbenzoate dimesylate provides 0.02% w/v of 4-(3-amino-1-(isoquinolin-6-ylamino)-1-oxopropan-2-yl)benzyl 2,4-dimethylbenzoate free base; and 0.0233% w/v/of 4-(3-amino-1-(isoquinolin-6-ylamino)-1-oxopropan-2-yl)benzyl 2,4-dimethylbenzoate diHCl provides 0.02% w/v of 4-(3-amino-1-(isoquinolin-6-ylamino)-1-oxopropan-2-yl)benzyl 2,4-dimethylbenzoate free base. (S)-4-(3-Amino-1-(isoquinolin-6-ylamino)-1-oxopropan-2-yl)benzyl 2,4-dimethylbenzoate dimesylate is also known as netarsudil mesylate.

In an embodiment, 4-(3-amino-1-(isoquinolin-6-ylamino)-1-oxopropan-2-yl)benzyl 2,4-dimethylbenzoate may be an enantiomerically enriched isomer of a stereoisomer. For example, the 4-(3-amino-1-(isoquinolin-6-ylamino)-1-oxopropan-2-yl)benzyl 2,4-dimethylbenzoate may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the (S)- or the (R)-enantiomer. Enantiomer, when used herein, refers to either of a pair of chemical compounds whose molecular structures have a mirror-image relationship to each other. In an embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

The term "pharmaceutically acceptable salt" includes salts of 4-(3-amino-1-(isoquinolin-6-ylamino)-1-oxopropan-2-yl)benzyl 2,4-dimethylbenzoate that are prepared with relatively nontoxic acids. Neutral forms of the compounds may be regenerated by contacting the salt with a base and isolating the parent compound in a conventional manner. The parent form of the compound differs from the various salt forms in certain physical properties, such as molecular weight and solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci.* Vol. 66, pp. 1-19. In an embodiment, the compound is present in mono-salt form. In embodiments, the compound is present in di-salt form.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, ethanesulfonic acid, methanesulfonic, mucic, oleic, oxalic, palmitic, pamoic, pantothenic, phenylacetic, phenylsulfonic, propionic, pyruvic, salicylic, stearic, succinic, sulfanilic, tartaric, p-toluenesulfonic, and valeric. Examples of suitable polymeric organic anions include, but are not limited to, those derived from the following polymeric acids: tannic acid, carboxymethyl cellulose.

b. Buffers

The ophthalmic compositions may comprise a buffer. The buffer may serve to minimize pH drift of the composition and help to stabilize the composition. Suitable buffers include, but are not limited to, acetic acid, citric acid, carbonic acid, phosphoric acid, boric acid, the pharmaceutically acceptable salts thereof, tromethamine, and combinations thereof. The buffer may be present in the ophthalmic composition in an amount of from about 0.01% weight/volume to about 1% weight/volume or about 0.1% w/v to about 0.9% w/v, or about 0.3% w/v to about 0.8% w/v, or about 0.4% w/v to about 0.6% w/v. Suitably, the buffer may be present in at least 0.01% w/v, at least 0.05% w/v, at least 0.1% w/v, at least 0.3% w/v, or at least 0.5% w/v. Suitably, the buffer may be present in an amount of no more than 1.0% w/v, no more than 0.8% w/v, or no more than 0.6% w/v. In embodiments, the buffer may be present in the ophthalmic composition in an amount of about 0.03% w/v, about 0.04% w/v, about 0.05% w/v, about 0.06% w/v, or about 0.07% w/v. The buffer may suitably be boric acid.

c. Tonicity Agents

The tonicity, or osmolality, of the composition can be adjusted to hypotonicity, isotonicity, or hypertonicity relative to normal tears by use of conventional materials known in the art. Tonicity agents are typically nonionic compounds. Examples of tonicity agents include, but are not limited to, sodium chloride, potassium chloride, mannitol, dextrose, glycerine, and propylene glycol. Suitably, the tonicity agent may be present in the ophthalmic composition in an amount of from about 0.01% weight/volume to about 10% weight/volume or about 1% w/v to about 10% w/v, or about 2.5% w/v to about 7.5% w/v, or about 4% w/v to about 6% w/v. Suitably, the tonicity agent may be present in at least 0.01% w/v, at least 0.05% w/v, at least 1% w/v, at least 2.5% w/v, at least 4% w/v, or at least 5% w/v. Suitably, the tonicity agent may be present in an amount of no more than 10% w/v, no more than 7.5% w/v, no more than 6% w/v, or no more than 5% w/v. In embodiments, the tonicity agent may be present in the ophthalmic composition in an amount of about 4.5% w/v, about 4.6% w/v, about 4.7% w/v, about 4.8% w/v, or about 4.9 w/v %. The tonicity agent may suitably be mannitol.

d. Other Components

In embodiments, the composition may also contain pH adjusting agents in an amount sufficient to adjust the pH of the composition to between about 3.5 and about 5.5. Suitably, the ophthalmic composition may have a pH of about 4.5 to about 5.2 or about 4.5 to about 5.1. In some embodiments, the ophthalmic composition has a pH of about 4.5, 4.6, 4.7, 4.8, 4.9, 5.0, 5.1, 5.2, or a range bounded by any two of these values. Suitable pH adjusting agents include, but are not limited to, sodium hydroxide.

In embodiments, the composition may also contain an emulsifying agent. Suitable emulsifying agents include, but are not limited to, polyoxyl 40 stearate, polyethoxylated castor oil, and combinations thereof, and other agents known to one skilled in the art. The emulsifying agent may be present in the ophthalmic composition in an amount of from about 0.01% weight/volume to about 1% weight/volume or about 0.1% w/v to about 0.9% w/v, or about 0.3% w/v to about 0.8% w/v, or about 0.4% w/v to about 0.6% w/v. Suitably, the emulsifying agent may be present in at least 0.01% w/v, at least 0.05% w/v, at least 0.1% w/v, at least 0.3% w/v, or at least 0.5% w/v. Suitably, the emulsifying agent may be present in an amount of no more than 1.0% w/v, no more than 0.8% w/v, or no more than 0.6% w/v. In embodiments, the emulsifying agent may be present in the ophthalmic composition in an amount of about 0.2% w/v, about 0.25% w/v, about 0.3% w/v, about 0.5% w/v, or about 0.75% w/v.

Ophthalmic compositions are typically packaged in unit dose or multidose form. Preservatives may be present to prevent or inhibit microbial contamination. Suitable preservatives include, but are not limited to, benzalkonium chloride, thimerosal, chlorobutanol, methyl paraben, propyl paraben, phenylethyl alcohol, edetate disodium, boric acid, sorbic acid, or other agents known to one skilled in the art. If present, the preservative may be present in the ophthalmic composition in an amount of about 0.001% w/v to about 1.0% w/v, or about 0.01% w/v to about 1.0% w/v, or about 0.1% w/v to about 1.0% w/v. Suitably, the preservative may be present in at least 0.001% w/v, at least 0.005% w/v, at least 0.01% w/v, at least 0.05% w/v, at least 0.1% w/v, or at least 0.5% w/v. Suitably, the preservative may be present in an amount of no more than 1.0% w/v, no more than 0.9% w/v, no more than 0.5% w/v, or no more than 0.1% w/v. In some embodiments, the preservative may be present in the ophthalmic composition in an amount of about 0.005% w/v, about 0.010% w/v, about 0.015% w/v, about 0.020% w/v, about 0.025% w/v, or about 0.030% w/v. The preservative may suitably be benzalkonium chloride.

In embodiments, the composition may comprise a second active pharmaceutical ingredient. The second active pharmaceutical ingredient may be a prostaglandin, such as latanoprost or travoprost. If present, the second active pharmaceutical ingredient may be present in an amount of about 0.001% w/v to about 1.0% w/v, or about 0.01% w/v to about 1.0% w/v, or about 0.1% w/v to about 1.0% w/v. Suitably, the second active pharmaceutical ingredient may be present in at least 0.001% w/v, at least 0.005% w/v at least 0.01% w/v, at least 0.05% w/v, at least 0.1% w/v, or at least 0.5% w/v, at least 5% w/v. Suitably, the second active pharmaceutical ingredient may be present in an amount of no more than 1.0% w/v, no more than 0.9% w/v, no more than 0.5% w/v, or no more than 0.1% w/v.

Other components commonly used in ophthalmic compositions, such as surfactants, comfort-enhancing agents, solubilizing agents, antioxidants, and stabilizing agents, may also be present.

Typically, the buffer and tonicity agent are mixed with or without the preservative. 4-(3-Amino-1-(isoquinolin-6-ylamino)-1-oxopropan-2-yl)benzyl 2,4-dimethylbenzoate dimesylate is then added to the mixture and stirred. Water is then added to bring the composition to 100%. The pH is then adjusted by adding pH adjusting agents.

3. FORMULATIONS AND METHODS OF USE

The ophthalmic formulations of the present disclosure may be formulated in various dosage forms suitable for topical ophthalmic delivery, including solutions, suspensions, emulsions, and gels. The compositions are suitably aqueous.

The present disclosure is also directed to methods of treating glaucoma and other ophthalmic diseases. As used herein, "treat" or "treating" as used herein refers to administering a regimen to the subject, e.g., the administration a compound or composition described herein, such that the disorder or at least one symptom of the disorder is healed, alleviated, relieved, altered, remedied, ameliorated, and/or improved. Treating includes administering an amount effective to alleviate, relieve, alter, remedy, ameliorate, improve and/or affect the disorder or the symptoms of the disorder. The treatment may inhibit deterioration or worsening of a symptom of a disorder.

The methods comprise topically applying to the affected eye(s) of the patient a therapeutically effective amount of a composition according to the present disclosure. The frequency and amount of dosage can be readily determined by one of skill in the art based on various clinical factors. The methods typically comprise topical application to the eye of one or two drops once or twice a day.

Thus, in one aspect, provided herein are methods of treating an ophthalmic disease in a subject in need thereof, the method comprising topically administering to an eye of a patient a composition provided herein. In some embodiments, the ophthalmic disease is glaucoma.

In some embodiments, provided herein are methods of treating glaucoma in a subject in need thereof, the method comprising topically administering to an eye of a patient an ophthalmic composition comprising: 4-(3-amino-1-(isoquinolin-6-ylamino)-1-oxopropan-2-yl)benzyl 2,4-dimethylbenzoate or a pharmaceutically acceptable salt thereof; about 0.01% weight/volume to about 1.0% weight/volume of a buffer; and about 0.01% weight/volume to about 10% weight/volume of a tonicity agent.

In some embodiments, provided herein are methods of treating glaucoma in a subject in need thereof, the method comprising topically administering to an eye of a patient an ophthalmic composition comprising: (S)-4-(3-amino-1-(isoquinolin-6-ylamino)-1-oxopropan-2-yl)benzyl 2,4-dimethylbenzoate or a pharmaceutically acceptable salt thereof; boric acid; and mannitol; wherein the composition has a pH from about 4.5 to about 5.2.

In some embodiments, provided herein are methods of treating glaucoma in a subject in need thereof, the method comprising topically administering to an eye of a patient an ophthalmic composition comprising: about 0.02% to about 0.03% weight/volume of (S)-4-(3-amino-1-(isoquinolin-6-ylamino)-1-oxopropan-2-yl)benzyl 2,4-dimethylbenzoate or a pharmaceutically acceptable salt thereof; about 4.7% weight/volume of mannitol; about 0.05% weight/volume of boric acid; and about 0.015% weight/volume of benzalkonium chloride; wherein the composition has a pH from about 4.5 to about 5.2.

In some embodiments, provided herein are methods of treating glaucoma in a subject in need thereof, the method comprising topically administering to an eye of a patient an ophthalmic composition comprising: (S)-4-(3-amino-1-(isoquinolin-6-ylamino)-1-oxopropan-2-yl)benzyl 2,4-dimethylbenzoate or a pharmaceutically acceptable salt thereof; boric acid; mannitol; and latanoprost.

In some embodiments, provided herein are methods of treating glaucoma in a subject in need thereof, the method comprising topically administering to an eye of a patient an ophthalmic composition comprising: mixture of (S)-4-(3-amino-1-(isoquinolin-6-ylamino)-1-oxopropan-2-yl)benzyl 2,4-dimethylbenzoate or a pharmaceutically acceptable salt thereof and (R)-4-(3-amino-1-(isoquinolin-6-ylamino)-1-oxopropan-2-yl)benzyl 2,4-dimethylbenzoate or a pharmaceutically acceptable salt thereof; boric acid; and mannitol; wherein the composition has a pH from about 4.5 to about 5.2.

In some embodiments, provided herein are methods of treating glaucoma in a subject in need thereof, the method comprising topically administering to an eye of a patient an ophthalmic composition comprising: about 0.02% to about 0.03% weight/volume of a mixture of (S)-4-(3-amino-1-(isoquinolin-6-ylamino)-1-oxopropan-2-yl)benzyl 2,4-dimethylbenzoate or a pharmaceutically acceptable salt thereof and (R)-4-(3-amino-1-(isoquinolin-6-ylamino)-1-oxopropan-2-yl)benzyl 2,4-dimethylbenzoate or a pharmaceutically acceptable salt thereof; about 4.7% weight/volume of mannitol; about 0.05% weight/volume of boric acid; and about 0.015% weight/volume of benzalkonium chloride; wherein the composition has a pH from about 4.5 to about 5.2.

In some embodiments, provided herein are methods of treating glaucoma in a subject in need thereof, the method comprising topically administering to an eye of a patient an ophthalmic composition comprising: a mixture of (S)-4-(3-amino-1-(isoquinolin-6-ylamino)-1-oxopropan-2-yl)benzyl 2,4-dimethylbenzoate or a pharmaceutically acceptable salt thereof and (R)-4-(3-amino-1-(isoquinolin-6-ylamino)-1- oxopropan-2-yl)benzyl 2,4-dimethylbenzoate or a pharmaceutically acceptable salt thereof; boric acid; mannitol; and latanoprost.

4. EMBODIMENTS

Embodiment 1. An ophthalmic composition, comprising: 4-(3-amino-1-(isoquinolin-6-ylamino)-1-oxopropan-2-yl) benzyl 2,4-dimethylbenzoate or its pharmaceutically acceptable salts; about 0.01% weight/volume to about 1.0% weight/volume of a buffer; and about 0.01% weight/volume to about 10% weight/volume of a tonicity agent.

Embodiment 2. The composition of embodiment 1, wherein the pH is from about 3.5 to about 5.5.

Embodiment 3. The composition of embodiments 1 or 2, wherein the pH is from about 4.5 to about 5.2.

Embodiment 4. The composition of any one of embodiments 1-3, further comprising a preservative.

Embodiment 5. The composition of embodiment 4, wherein the preservative comprises benzalkonium chloride.

Embodiment 6. The composition of any one of embodiments 1-5, further comprising an emulsifying agent.

Embodiment 7. The composition of embodiment 6, wherein the emulsifying agent comprises polyoxyl 40 stearate, polyethoxylated castor oil, or a combination thereof.

Embodiment 8. The composition of any one of embodiments 1-7, wherein the tonicity agent comprises mannitol.

Embodiment 9. The composition of any one of embodiments 1-8, wherein the buffer comprises boric acid or its salts.

Embodiment 10. The composition of any one of embodiments 1-9, further comprising water.

Embodiment 11. The composition of any one of embodiments 1-10, further comprising a pH adjusting agent.

Embodiment 12. The composition of any one of embodiments 1-11, wherein the 4-(3-amino-1-(isoquinolin-6-ylamino)-1-oxopropan-2-yl)benzyl 2,4-dimethylbenzoate is a dimesylate salt.

Embodiment 13. The composition of any one of embodiments 1-12, wherein the 4-(3-amino-1-(isoquinolin-6-ylamino)-1-oxopropan-2-yl)benzyl 2,4-dimethylbenzoate or its pharmaceutically acceptable salts is (S)-4-(3-amino-1-(isoquinolin-6-ylamino)-1-oxopropan-2-yl)benzyl 2,4-dimethylbenzoate or its pharmaceutically acceptable salts.

Embodiment 14. The composition of any one of embodiments 1-13, further comprising a second ophthalmic active compound.

Embodiment 15. The composition of embodiment 14, wherein the second ophthalmic active compound is a prostaglandin analog.

Embodiment 16. The composition of embodiment 15, wherein the prostaglandin analog is latanoprost or travoprost.

Embodiment 17. The composition of any one of embodiments 1-16, comprising about 0.02% w/v to about 0.03% w/v of 4-(3-amino-1-(isoquinolin-6-ylamino)-1-oxopropan-2-yl)benzyl 2,4-dimethylbenzoate or it pharmaceutically acceptable salts.

Embodiment 18. The composition of any one of embodiments 1-17, comprising about 4.7% weight/volume of mannitol.

Embodiment 19. The composition of any one of embodiments 1-18, comprising about 0.05% weight/volume of boric acid.

Embodiment 20. The composition of any one of embodiments 1-19, comprising about 0.015% weight/volume of benzalkonium chloride.

Embodiment 21. The composition of embodiment 16, further comprising 0.005% weight/volume of latanoprost or travoprost.

Embodiment 22. An ophthalmic composition, comprising: (S)-4-(3-amino-1-(isoquinolin-6-ylamino)-1-oxopropan-2-yl)benzyl 2,4-dimethylbenzoate or its pharmaceutically acceptable salts; boric acid; and mannitol; wherein the composition has a pH from about 4.5 to about 5.2.

Embodiment 23. An ophthalmic composition comprising: about 0.02% to about 0.03% weight/volume of (S)-4-(3-amino-1-(isoquinolin-6-ylamino)-1-oxopropan-2-yl)benzyl 2,4-dimethylbenzoate or its pharmaceutically acceptable salts; about 4.7% weight/volume of mannitol; about 0.05% weight/volume of boric acid; and about 0.015% weight/volume of benzalkonium chloride; wherein the composition has a pH from about 4.5 to about 5.2.

Embodiment 24. An ophthalmic composition, comprising: (S)-4-(3-amino-1-(isoquinolin-6-ylamino)-1-oxopropan-2-yl)benzyl 2,4-dimethylbenzoate or its pharmaceutically acceptable salts; boric acid; mannitol; and latanoprost.

Embodiment 25. The compositions of any one of embodiments 22-24 wherein the salt is the dimesylate salt.

Embodiment 26. A method of treating an ophthalmic disease, the method comprising topically administering to the eye of a patient in need a composition of any one of claims 1-24.

Embodiment 27. The method of embodiments 26, wherein the ophthalmic disease is glaucoma.

5. EXAMPLES

The present disclosure has multiple aspects, illustrated by the following non-limiting examples. In the various examples, the below materials and characterization techniques have been used.

Example 1. Formulations of 4-(3-amino-1-(isoquinolin-6-ylamino)-1-oxopropan-2-yl)benzyl 2,4-dimethylbenzoate Table 1 shows the composition of 4-(3-amino-1-(isoquinolin-6-ylamino)-1-oxopropan-2-yl)benzyl 2,4-dimethylbenzoate formulations. Formulations N, O, and P were prepared by adding boric acid, d-mannitol, and with or without 0.015% benzalkonium chloride in a labeled 150-milliliter (mL) plastic storage container. 4-(3-amino-1-(isoquinolin-6-ylamino)-1-oxopropan-2-yl)benzyl 2,4-dimethylbenzoate dimesylate, with or without 5% benzalkonium chloride stock solution, was then added and dissolved by stirring the solution for another 10 minutes. 100 milliliter (mL) of purified water was then added to bring the solution almost to 100%, and the pH was adjusted to approximately 5.0. Sufficient 4-(3-amino-1-(isoquinolin-6-ylamino)-1-oxopropan-2-yl)benzyl 2,4-dimethylbenzoate dimesylate (CAS number: #1422144-42-0) (0.0285% w/v) was added to have 4-(3-amino-1-(isoquinolin-6-ylamino)-1-oxopropan-2-yl) benzyl 2,4-dimethylbenzoate free base (CAS number: #1254032-66-0) present at 0.02% w/v.

TABLE 1

| Ingredient | Formulation (% weight/volume) | | |
|---|---|---|---|
| | N | O | P |
| 4-(3-amino-1-(isoquinolin-6-ylamino)-1-oxopropan-2-yl)benzyl 2,4-dimethylbenzoate free base | 0.02 | 0.02 | 0.04 |
| Boric acid | 0.05 | 0.05 | 0.05 |
| D-mannitol | 4.7 | 4.7 | 4.7 |
| Benzalkonium chloride | — | 0.015 | 0.015 |
| Purified water | q.s. | q.s. | q.s. |
| pH | 5.0 | 5.0 | 5.0 |

Example 2. Formulations of Fixed-Dose Combination of 4-(3-amino-1-(isoquinolin-6-ylamino)-1-oxopropan-2-yl)benzyl 2,4-dimethylbenzoate and Latanoprost Table 2 shows the formulations of fixed-dose combination of 4-(3-amino-1-(isoquinolin-6-ylamino)-1-oxopropan-2-yl)benzyl 2,4-dimethylbenzoate and latanoprost. Formulations R and S were prepared by adding boric acid and d-mannitol in a labeled 150-milliliter (mL) plastic storage container. 4-(3-amino-1-(isoquinolin-6-ylamino)-1-oxopropan-2-yl)benzyl 2,4-dimethylbenzoate and benzalkonium chloride/latanoprost stock solution (100×) were then added and dissolved by stirring the solution for another 10 minutes. 100 milliliter (mL) of purified water was then added to bring the solution almost to 100%, and the pH was adjusted to approximately 5.0. Sufficient 4-(3-amino-1-(isoquinolin-6-ylamino)-1-oxopropan-2-yl)benzyl 2,4-dimethylbenzoate dimesylate (CAS number: #1422144-42-0) (0.0285% w/v) was added to have 4-(3-amino-1-(isoquinolin-6-ylamino)-1-oxopropan-2-yl)benzyl 2,4-dimethylbenzoate free base (CAS number: #1254032-66-0) present at 0.02% w/v.

TABLE 2

| Ingredient | Formulation (% weight/volume) | |
|---|---|---|
| | R | S |
| 4-(3-amino-1-(isoquinolin-6-ylamino)-1-oxopropan-2-yl)benzyl 2,4-dimethylbenzoate free base | 0.02 | 0.02 |
| Latanoprost | 0.005 | 0.005 |
| Boric acid | 0.05 | 0.05 |
| D-mannitol | 4.7 | 4.7 |
| Benzalkonium chloride | 0.015 | 0.02 |
| Purified water | q.s. | q.s. |
| pH | 5.0 | 5.0 |

Example 3. Preservative-Free, Fixed-Dose Combination 4-(3-amino-1-(isoquinolin-6-ylamino)-1-oxopropan-2-yl)benzyl 2,4-dimethylbenzoate and Latanoprost Additional formulations may be prepared according to the method in Example 1. Table 3 shows the formulations of preservative-free, fixed-dose combination of 4-(3-amino-1-(isoquinolin-8-ylamino)-1-oxopropan-2-yl)benzyl 2,4-dimethylbenzoate and latanoprost.

TABLE 3

| Ingredient | Formulation (% weight/volume) | | |
|---|---|---|---|
| | T | U | V |
| 4-(3-amino-1-(isoquinolin-6-ylamino)-1-oxopropan-2-yl)benzyl 2,4-dimethylbenzoate free base | 0.02 | 0.02 | 0.02 |
| Latanoprost | 0.005 | 0.005 | 0.005 |
| Boric acid | 0.05 | 0.05 | 0.05 |
| D-mannitol | 4.7 | 4.7 | 4.7 |
| Polyoxyl 40 stearate (Myrj-52) | 0.5 | — | — |
| Cremophor RH 40 | — | 0.25 | 0.5 |
| Benzalkonium chloride | — | — | — |
| Purified water | q.s. | q.s. | q.s. |
| pH | 5.5 | 5.5 | 5.5 |

Example 4. Formulations of 4-(3-amino-1-(isoquinolin-6-ylamino)-1-oxopropan-2-yl)benzyl 2,4-dimethylbenzoate Table 4 shows compositions of 4-(3-amino-1-(isoquinolin-6-ylamino)-1-oxopropan-2-yl)benzyl 2,4-dimethylbenzoate formulations as its dimesylate and diHCl salts. Formulations N4 and O4 were prepared by adding boric acid, d-mannitol, and with or without 0.015% benzalkonium chloride in a labeled 150-milliliter (mL) plastic storage container. The disalts 4-(3-amino-1-(isoquinolin-6-ylamino)-1-oxopropan-2-yl)benzyl 2,4-dimethylbenzoate mesylate (CAS number: #1422144-42-0), or 4-(3-amino-1-(isoquinolin-6-ylamino)-1-oxopropan-2-yl)benzyl 2,4-dimethylbenzoate chloride (CAS number: #1253952-02-1), with or without 5% benzalkonium chloride stock solution, was then added and dissolved by stirring the solution for another 10 minutes. 100 milliliter (mL) of purified water was then added to bring the solution almost to 100%, and the pH was adjusted to approximately 5.0.

Formulation P4 may be prepared according to the process described herein.

TABLE 4

| Ingredient | Formulation (% weight/volume) | | |
|---|---|---|---|
| | N4 | O4 | P4 |
| 4-(3-amino-1-(isoquinolin-6-ylamino)-1-oxopropan-2-yl)benzyl 2,4-dimethylbenzoate mesylate (disalt) | 0.0285 | 0.000 | 0.0143 |
| 4-(3-amino-1-(isoquinolin-6-ylamino)-1-oxopropan-2-yl)benzyl 2,4-dimethylbenzoate HCl (disalt) | 0.000 | 0.0233 | 0.0116 |
| Boric acid | 0.05 | 0.05 | 0.05 |
| D-mannitol | 4.7 | 4.7 | 4.7 |
| Benzalkonium chloride | 0.015 | 0.015 | 0.008 |
| Purified water | q.s. | q.s. | q.s. |
| pH | 5.0 | 4.8 | 4.9 |

It is understood that the foregoing detailed description and accompanying examples are merely illustrative and are not to be taken as limitations upon the scope of the disclosure, which is defined solely by the appended claims and their equivalents.

We claim:

1. An ophthalmic formulation, consisting of:
   0.0285 weight/volume % of a dimesylate salt of 4-(3-amino-1-(isoquinolin-6-ylamino)-1-oxopropan-2-yl)benzyl 2,4-dimethylbenzoate;

0.05 weight/volume % of boric acid;
4.7 weight/volume % of mannitol;
water; and
a pH of 5.

2. The ophthalmic formulation of claim 1, wherein the 4-(3-amino-1-(isoquinolin-6-ylamino)-1-oxopropan-2-yl)benzyl 2,4-dimethylbenzoate is (S)-4-(3-amino-1-(isoquinolin-6-ylamino)-1-oxopropan-2-yl)benzyl 2,4-dimethylbenzoate.

3. The ophthalmic formulation of claim 1, wherein the mannitol is D-mannitol.

4. The ophthalmic formulation of claim 1, which is a topical ophthalmic formulation.

5. The ophthalmic formulation of claim 1, which is packaged in a unit dose form.

6. The ophthalmic formulation of claim 1, which is packaged in a multidose form.

7. The ophthalmic formulation of claim 1, which is in a plastic storage container.

8. The ophthalmic formulation of claim 1, consisting of:
   0.0285 weight/volume % of a dimesylate salt of (S)-4-(3-amino-1-(isoquinolin-6-ylamino)-1-oxopropan-2-yl)benzyl 2,4-dimethylbenzoate,
   0.05 weight/volume % of boric acid,
   4.7 weight/volume % of D-mannitol,
   water, and
   a pH of 5.

9. A method of treating glaucoma in a subject in need thereof, comprising topically administering to an eye of the subject an ophthalmic formulation consisting of:
   0.0285 weight/volume % of a dimesylate salt of 4-(3-amino-1-(isoquinolin-6-ylamino)-1-oxopropan-2-yl)benzyl 2,4-dimethylbenzoate,
   0.05 weight/volume % of boric acid,
   4.7 weight/volume % of mannitol,
   water, and
   a pH of 5.

10. The method of claim 9, wherein the 4-(3-amino-1-(isoquinolin-6-ylamino)-1-oxopropan-2-yl)benzyl 2,4-dimethylbenzoate is (S)-4-(3-amino-1-(isoquinolin-6-ylamino)-1-oxopropan-2-yl)benzyl 2,4-di methyl benzoate.

11. The method of claim 9, wherein the mannitol is D-mannitol.

12. The method of claim 9, wherein the ophthalmic formulation is a topical ophthalmic formulation.

13. The method of claim 9, wherein the ophthalmic formulation is packaged in a unit dose form.

14. The method of claim 9, wherein the ophthalmic formulation is packaged in a multidose form.

15. The method of claim 9, wherein the ophthalmic formulation is in a plastic storage container.

16. The method of claim 9, wherein the ophthalmic formulation consists of:
   0.0285 weight/volume % of a dimesylate salt of (S)-4-(3-amino-1-(isoquinolin-6-ylamino)-1-oxopropan-2-yl)benzyl 2,4-dimethylbenzoate,
   0.05 weight/volume % of boric acid,
   4.7 weight/volume % of D-mannitol,
   water, and
   a pH of 5.

* * * * *